(12) United States Patent
Sahatjian et al.

(10) Patent No.: US 10,238,442 B2
(45) Date of Patent: Mar. 26, 2019

(54) BALLOON EXPANDABLE CEMENT DIRECTOR AND RELATED METHODS

(71) Applicant: GLOBUS MEDICAL, INC., Audubon, PA (US)

(72) Inventors: Ronald Sahatjian, Lexington, MA (US); Andrew R. Sennett, Hanover, MA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 14/811,878

(22) Filed: Jul. 29, 2015

(65) Prior Publication Data

US 2015/0335370 A1 Nov. 26, 2015

Related U.S. Application Data

(63) Continuation of application No. 13/035,423, filed on Feb. 25, 2011, now Pat. No. 9,126,023.

(Continued)

(51) Int. Cl.

| | |
|---|---|
| *A61B 17/56* | (2006.01) |
| *A61B 17/88* | (2006.01) |
| *A61M 25/10* | (2013.01) |
| *A61B 17/70* | (2006.01) |
| *A61F 2/46* | (2006.01) |
| *A61B 17/00* | (2006.01) |

(52) U.S. Cl.
CPC ...... *A61B 17/8811* (2013.01); *A61B 17/7098* (2013.01); *A61B 17/8819* (2013.01); *A61B 17/8855* (2013.01); *A61M 25/10* (2013.01); *A61B 17/8802* (2013.01); *A61B 2017/00867* (2013.01); *A61F 2/4601* (2013.01); *A61M 25/1002* (2013.01); *A61M 25/1018* (2013.01); *A61M 25/10181* (2013.11); *A61M 2025/1075* (2013.01); *A61M 2025/1084* (2013.01)

(58) Field of Classification Search
CPC .......... A61F 2/4601; A61F 2002/2835; A61B 17/8822
USPC ...... 606/63, 86 R, 92–94, 99, 105; 604/96.01, 103.01–103.02, 103.06, 604/103.07, 103.09, 103.11–103.14
See application file for complete search history.

(56) References Cited

U.S. PATENT DOCUMENTS

| | | | |
|---|---|---|---|
| 6,451,052 B1 * | 9/2002 | Burmeister | A61F 2/844 623/1.16 |
| 2005/0261781 A1 * | 11/2005 | Sennett | A61B 17/7098 623/23.54 |

(Continued)

FOREIGN PATENT DOCUMENTS

WO 9531945 A1 11/1995

*Primary Examiner* — Zade Coley
*Assistant Examiner* — Jessica Weiss

(57) ABSTRACT

The invention relates to a cement director for insertion within a vertebral body or other body structure, and related methods of use. An example method includes creating a cavity in a vertebral body, inserting a collapsible mesh structure into the cavity in a collapsed state, wherein the collapsible mesh structure comprises regions of different permeability to a bone cement, inflating a balloon within the collapsible mesh structure to expand the mesh structure, and injecting a bone cement into the mesh structure, wherein the bone cement flows preferentially out of the mesh structure through at least one region of greater permeability.

20 Claims, 12 Drawing Sheets

Related U.S. Application Data

(60) Provisional application No. 61/308,055, filed on Feb. 25, 2010.

(56) References Cited

U.S. PATENT DOCUMENTS

| | | |
|---|---|---|
| 2007/0088436 A1 | 4/2007 | Parsons et al. |
| 2007/0093899 A1* | 4/2007 | Dutoit .................. A61B 17/686 623/17.11 |
| 2008/0195081 A1 | 8/2008 | Moll |
| 2008/0208320 A1* | 8/2008 | Tan-Malecki ...... A61B 17/1617 623/1.17 |

* cited by examiner

SECTION A--A

BALLOON EXPANDABLE CEMENT DIRECTOR AND RELATED METHODS

CROSS-REFERENCE TO RELATED APPLICATIONS

This application is a continuation of U.S. patent application Ser. No. 13/035,423, filed Feb. 25, 2011, which claims priority to U.S. provisional patent application No. 61/308,055, filed Feb. 25, 2010, the disclosures of which are hereby incorporated herein by reference in their entireties for all purposes. This application is also related to U.S. Pat. No. 7,465,310, issued Dec. 16, 2008, U.S. patent application Ser. No. 12/241,979, filed Sep. 30, 2008, U.S. patent application Ser. No. 11/957,022, filed Dec. 14, 2007, U.S. patent application Ser. No. 11/957,039, filed Dec. 14, 2007, U.S. patent application Ser. No. 12/486,439, filed Jun. 17, 2009, and U.S. provisional patent application No. 61/210,771, filed Mar. 23, 2009, the disclosures of all of which are being incorporate herein by reference in their entirety.

FIELD OF THE INVENTION

The present invention relates generally to the field of orthopedic devices, and more particularly to systems and related methods for injection of bone cement into vertebral bodies to facilitate treatment of a vertebral compression fracture.

BACKGROUND OF THE INVENTION

There are many disease states that cause bone defects in the spinal column. For instance, osteoporosis and other metabolic bone conditions weaken the bone structure and predispose the bone to fracture. If not treated, certain fractures and bone defects of the vertebral body may produce intolerable pain, and may lead to the development of deformity and severe medical complications.

Bone weakening may also result from benign or malignant lesions of the spinal column. Tumors often compromise the structural integrity of the bone and thus require surgical stabilization and repair of defects with biocompatible materials such as bone grafts or cements. Bone tumors of the spine are relatively common, and many cause vertebral compression fracture.

More than 700,000 osteoporotic compression fractures of the vertebrae occur each year in the United States—primarily in the elderly female population. Until recently, treatment of such fractures was limited to conservative, non-operative therapies such as bed rest, bracing, and medications.

One surgical technique for treating a vertebral compression fracture, including injecting or filling the fracture bone or bone defect with biocompatible bone cement, is called "vertebroplasty." This technique was developed in the mid 1980's to address the inadequacy of conservative treatment for vertebral body fracture. This procedure involves injecting radio-opaque bone cement directly into a fracture void, through a minimally invasive cannula or needle, under fluoroscopic control. The cement is pressurized by a syringe or similar plunger mechanism, thus causing the cement to fill the void and penetrate the interstices of a broken trabecular bone. Once cured, the cement stabilizes the fracture and eliminates or reduces pain. Bone cements are generally formulations of non-resorbable biocompatible polymers such as PMMA (polymethylmethacrylate), or resorbable calcium phosphate cements which allow for the gradual replacement of the cement with living bone. Both types of bone cements have been used successfully in the treatment of bone defects secondary to compression fractures of the vertebral body.

One clinical issue associated with vertebroplasty is containment of the cement within the margins of the defect. For instance, an osteoporotic compression fracture usually compromises portions of the cortical bone creating pathways to cement leakage. Thus, there is a risk of cement flowing beyond the confines of the bone into the body cavity. Cement leakage into the spinal canal, for instance, can have grave consequences to the patient.

Yet another significant risk associated with vertebroplasty is the injection of cement directly into the venous system, since the veins within the vertebral body are larger than the tip of the needle used to inject the cement. A combination of injection pressure and inherent vascular pressure may cause unintended uptake of cement into the pulmonary vessel system, with potentially disastrous consequences including embolism to the lungs.

One technique which has gained popularity in recent years is a modified vertebroplasty technique in which a "balloon tamp" is inserted into the vertebral body via a cannula approach to expand or distract the fractured bone and create a void within the cancellous structure. Balloon tamps are inflated using pressurized fluid such as saline solution. The inflation of a balloon membrane produces radial forces on the surface of the membrane and forms a cavity in the bone. When deflated and removed, the membrane leaves a cavity that is subsequently filled with bone cement. The formation of a cavity within the bone allows for the injection of more viscous cement material, which may be relatively less prone to leakage.

In certain instances, such as the treatment of acute or mobile fractures, the balloon is also effective at "reducing" the fracture and restoring anatomic shape to a fractured body. In particular, balloon dilatation in bone is maximally effective if the balloon device is targeted inferior to, or below, the fracture plane. In this instance, the balloon dilatation may distract, or lift, a fracture bone fragment, such as the vertebral body endplate.

In other instances, such as chronic or partially healed fractures, balloons are less effective at "reducing" the fracture because radial forces are insufficient. Often the bone in an incompletely healing fracture is too dense and strong, and requires more aggressive cutting treatment, such as a drill or reamer tool to create a sufficient cavity. In these more challenging cases, injecting bone cement into a cavity created by a balloon or a reamer in the vicinity of the fracture is not always sufficient to stabilize the bone and relieve pain, even in the absence of fracture reduction. While fracture reduction may be desirable, prior methods of implementing fracture reduction using a balloon have generally been ineffective.

SUMMARY OF THE INVENTION

The present invention is directed towards novel methods and devices for directing bone cement into a vertebral body. The methods and devices disclosed herein may include a cement director and, for example, an at least partially balloon expandable cement director, for insertion into a vertebral body to assist in controlling the injection of bone cement used, for example, to stabilize vertebral compression fractures.

One aspect of the invention relates to a method of treating a vertebral body including the steps of creating a cavity in a vertebral body, inserting a collapsible mesh structure into the cavity in a collapsed state, wherein the collapsible mesh structure includes regions of different permeability to a bone cement, inflating a balloon within the collapsible mesh structure to expand the mesh structure, and injecting a bone cement into the mesh structure, wherein the bone cement flows preferentially out of the mesh structure through at least one region of greater permeability.

In one embodiment, the mesh structure includes a plurality of layers. The mesh structure may include a first layer including, or consisting essentially of, a first shape memory material in an austenite phase at body temperature (e.g., approximately 100° F.), a second layer including, or consisting essentially of, a second shape memory material in a martensite phase at body temperature and, optionally, a covering layer. In one embodiment, the mesh structure includes a shape memory material such as, but not limited to, nickel titanium (Ni—Ti). The shape memory material may be formed in an austenite phase at body temperature.

In one embodiment the surface of the mesh structure is covered by a covering layer. The covering layer may be impermeable, or substantially impermeable, to the bone cement. The covering layer may include an elastic material. The elastic material may include, or consist essentially of, silicone, polyurethane, styrene, isobutylene, polyester, nylon, natural fiber material, and/or combinations thereof. In one embodiment, the covering layer covers at least one of an interior surface and an exterior surface of the mesh structure. The at least one region of greater permeability may include, or consist essentially of, one or more regions that are not covered by the covering layer. In one embodiment, the covering layer includes a textile such as, but not limited to, a knitted fabric, a braided fabric, and/or a woven fabric.

In one embodiment, the at least one region of greater permeability includes, or consists essentially of, at least one hole in a wall of the mesh structure. In one embodiment, the collapsible mesh structure is at least partially self-expandable from its collapsed state. The balloon may be inserted into the interior of the mesh structure prior to the mesh structure being inserted into the cavity. One embodiment of the method further includes deflating the inflated balloon, wherein the mesh structure maintains an expanded form upon deflation of the balloon, and removing the deflated balloon from the collapsible mesh structure. The balloon may be inflated with sufficient pressure to move endplates of the vertebral body apart. The mesh structure may be expanded to about a boundary of the cavity.

Another aspect of the invention includes a collapsible device for insertion into a cavity in a vertebral body. The collapsible device includes at least one boundary wall having a closed distal end and an open proximal end adapted to releasably couple to a deployment device. The boundary wall includes a mesh structure having a first layer including, or consisting essentially of, a first shape memory material in an austenite phase at body temperature, a second layer including, or consisting essentially of, a second shape memory material in a martensite phase at body temperature, a cover layer, and at least one region of different permeability to a bone cement.

One or both of the shape memory materials may include, or consist essentially of, nickel titanium. The covering layer may cover the surface of the mesh structure and may be impermeable to bone cement. In one embodiment, the covering layer includes, or consists essentially of, an elastic material. The elastic material may include, or consist essentially of, silicone, polyurethane, styrene, isobutylene, polyester, nylon, natural fiber material, and/or combinations thereof. The covering layer may cover at least one of an interior surface and an exterior surface of the mesh structure. The at least one region of greater permeability may include, or consist essentially of, one or more regions that are not covered by the covering layer.

The covering layer may include, or consist essentially of, a textile such as, but not limited to, a knitted fabric, a braided fabric and/or a woven fabric. The at least one region of greater permeability may include, or consist essentially of, at least one hole in one or more layers of the mesh structure. The collapsible mesh structure may be at least partially self-expandable.

Yet another aspect of the invention includes a system for deploying a collapsible device into a cavity formed in a vertebral body. The system may include a delivery device including a distal end for insertion into a vertebral body and a proximal end including a handle, means for releasably coupling a collapsible implant to the distal end of the delivery device, and a balloon coupled at the distal end of the delivery device and adapted to expand the collapsible implant when disposed therein. The collapsible implant may include a first layer including, or consisting essentially of, a first shape memory material formed in an austenite phase, a second layer including, or consisting essentially of, a second shape memory material formed in a martensite phase, a cover layer, and one or more regions of different permeability to a bone cement.

In one embodiment, the system may include a push rod adapted to be removably insertable through the delivery device and into the implant to hold the implant in a collapsed configuration prior to deployment. In one embodiment, the system may include a sheath adapted to removably extend through the delivery device and over the implant to hold the implant in a collapsed configuration prior to deployment.

Yet another aspect of the invention includes an expandable device for insertion into a cavity in a vertebral body. The device includes at least one mesh structure including, or consisting essentially of, a first shape memory material in a martensite phase at body temperature. The mesh structure includes a closed distal end, an open proximal end adapted to releasably couple to a deployment device, and at least one region of different permeability to a bone cement. The mesh structure is expandable from an unexpanded configuration to an expanded configuration by expansion of a balloon within an interior of the mesh structure, and the mesh structure is adapted to maintain the expanded configuration after removal of the balloon from the interior of the mesh structure.

In one embodiment, the shape memory material includes, or consists essentially of, nickel titanium. The mesh structure may also include a second layer including, or consisting essentially of, a second shape memory material in an austenite phase at body temperature.

In one embodiment, the mesh structure may further include a covering layer. The covering layer may be impermeable to bone cement. The covering layer may include, or consist essentially of, an elastic material. The elastic material may be selected from materials such as, but not limited to, silicone, polyurethane, styrene, isobutylene, polyester, nylon, natural fiber material, and/or combinations thereof. The covering layer may cover at least one of an interior surface and an exterior surface of the mesh structure. The covering layer may include, or consist essentially of, a textile selected from the group consisting of a knitted fabric, a braided fabric, and/or a woven fabric. In one embodiment, at least one region of greater permeability comprises a region that is not covered by the covering layer. In one embodiment, the at least one region of greater permeability may include, or consist essentially of, at least one hole in one or more layers of the mesh structure.

In one embodiment, the mesh structure is expandable only by expansion of an expansion element, such as, but not limited to, a balloon. In an alternative embodiment, the mesh structure is at least partially self-expandable.

Yet another aspect of the invention includes a system for deploying an expandable device into a cavity formed in a vertebral body. The system includes a delivery device including a distal end for insertion into a vertebral body and a proximal end including a handle, means for releasably coupling an expandable device to the distal end of the delivery device, and a balloon coupled at the distal end of the delivery device and adapted to expand the collapsible implant when disposed therein. The expandable device may include a shape memory material in a martensite phase at body temperature, a closed distal end, an open proximal end, and at least one region of different permeability to a bone cement.

In one embodiment, the system includes a push rod adapted to be removably insertable through the delivery device and into the expandable device to hold the expandable device in a collapsed configuration prior to deployment. In one embodiment, the system includes a sheath adapted to removably extend through the delivery device and over the expandable device to hold the expandable device in a collapsed configuration prior to deployment.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION OF THE INVENTION

Figure 1:
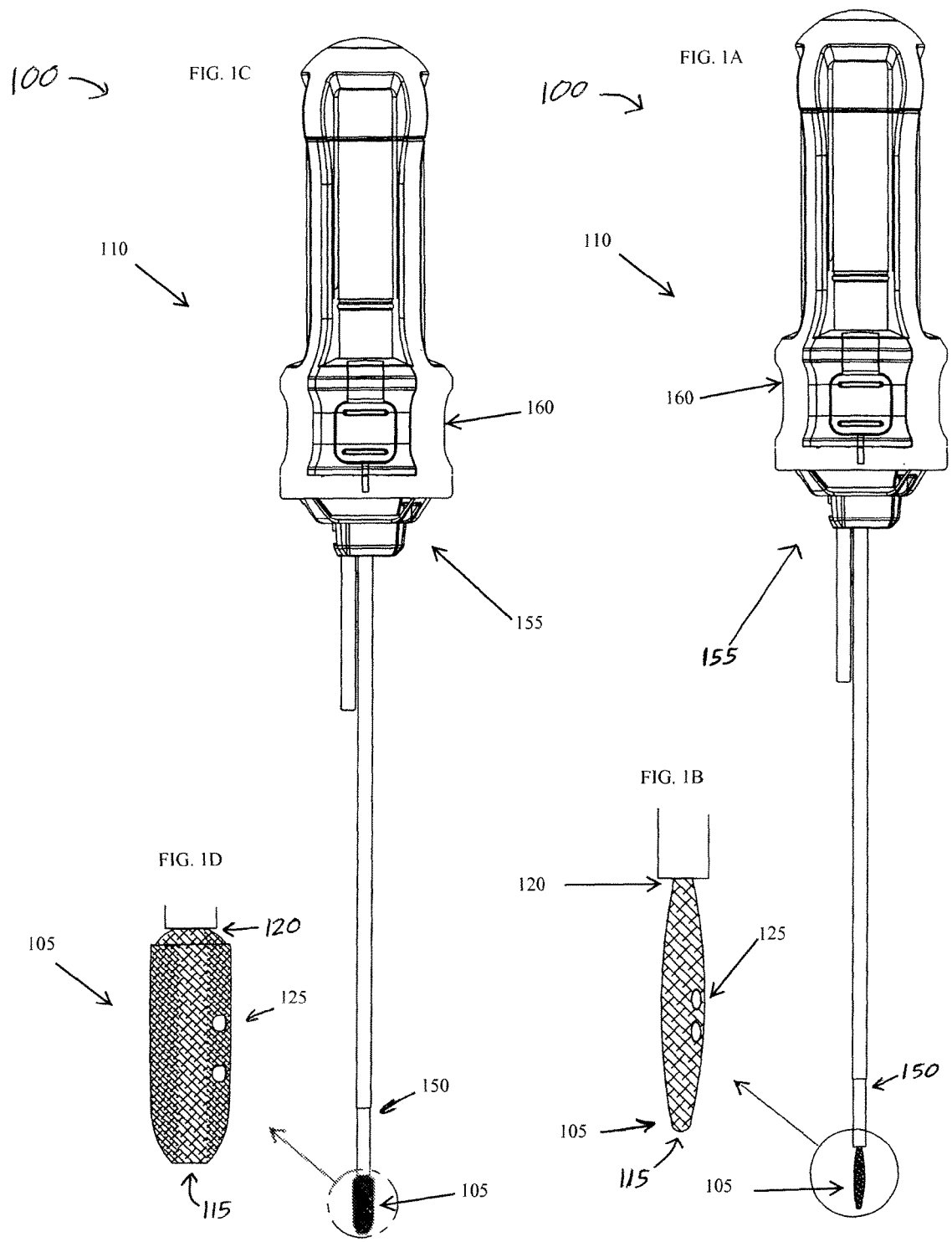
FIG. 1A is a schematic side view of a cement director and associated deployment system prior to expansion of the cement director, in accordance with one embodiment of the invention.
FIG. 1B is a schematic side view of the unexpanded cement director of FIG. 1A.
FIG. 1C is a schematic side view of the cement director and associated deployment system of FIG. 1A after expansion of the cement director, in accordance with one embodiment of the invention.
FIG. 1D is a schematic side view of the expanded cement director of FIG. 1C.

Various embodiments of the invention relate to balloon expandable cement directors and at least partially self-expanding balloon expandable cement directors for insertion into a vertebral body or other bodily area, and related systems and methods of deployment.

An example system for delivering and deploying a cement director is shown in FIGS. 1A to 1D. In this embodiment, the system 100 includes a mesh structure, e.g., a stent or cement director 105, releasably coupled to a delivery and deployment system 110. The cement director 105 may, for example, be at least partially balloon expandable with, for example, a standard angioplasty balloon catheter. The cement director 105 is shown in a collapsed form (i.e., prior to expansion) in FIGS. 1A and 1B, and in an expanded form (i.e., after expansion) in FIGS. 1C and 1D. An example deployment system 110 for use with the cement directors disclosed herein is described in U.S. patent application Ser. No. 11/957,039, filed Dec. 14, 2007, the disclosure of which is incorporated herein by reference in its entirety.

The delivery and deployment system 100 may include a distal end 150 for insertion into a vertebral body and a proximal end 155 comprising a handle 160, means for releasably coupling a collapsible implant to the distal end 150 of the delivery device, and a balloon coupled at the distal end of the delivery device and adapted to expand a collapsible implant, e.g., the cement director 105, when disposed therein.

In one embodiment, the cement director 105 has an outer diameter of about 2-4 mm and a length of about 15-25 mm when in collapsed form. In various embodiment, the length of the cement director 105 may be 15 mm, 20 mm, or 25 mm, depending upon the size of the vertebral body into which it is to be placed. In an alternative embodiment, the length of the cement director 105 may be greater or lesser, as appropriate. In alternative embodiments, the outer diameter, when collapsed, may be greater or lesser, depending upon the size of the vertebral body and/or the size of the cannula through which it is inserted into the interior of the vertebral body. The cement director 105 may be formed from materials including, but not limited to, metals (such as stainless steel), alloys (such as Ni—Ti), and/or plastics.

In one embodiment, the cement director 105 can expand by up to about 400% to 500%, or more, of its collapsed diameter, depending, for example, upon the materials used, the geometry of the cement director 105, the balloon being used to expand the cement director 105, and/or the size of the vertebral body into which it is to be placed. For example, in one embodiment, the cement director 105 can expand to an outer diameter of between 11 mm to 15 mm, and even up to about 17 mm. In alternative embodiments, the cement director 105 may be adapted to expand to a greater or lesser extent, e.g., down to about 10 mm or less and up to about 20 mm or more. For example, various cement directors 105 may be adapted to expand to between 200 and 600% of their collapsed diameter.

In one embodiment, the cement director 105 includes a closed distal end 115 and an open proximal end 120, with the open proximal end 120 releasably coupled to a distal end of a fill passageway of the deployment system 110 through which, for example, a balloon can be inserted and removed, and/or cement can be injected into the interior of the cement director 105. The closed distal end 115 may be formed, for example, by welding, or otherwise attaching, the distal ends of the struts of an open stent together to seal an end of the stent. In one embodiment, the open proximal end 120 may have a diameter of approximately 2-4 mm.

The cement director 105 may be covered with a covering material such as, but not limited to, a polymer. Example materials may include, or consist essentially of, silicone, polyurethane, styrene, isobutylene, polyester, nylon, natural fiber material, and/or combinations thereof. In one embodiment, the material may be one or more textiles such as, but not limited to, a knitted fabric, a braided fabric, and/or a woven fabric. The covering layer may cover at least one of an interior surface and an exterior surface of the cement director 105. In one embodiment, the covering material may include, or consist essentially of, a mesh. This mesh may, for example, be impregnated with a material such as, but not limited to, an elastomeric polymer.

The surface of the cement director 105 may include one or more regions of greater permeability 125. These regions of greater permeability 125 may, for example, be holes created in the surface to allow a bone cement injected into the interior of the cement director 105 to flow preferentially out of the cement director 105 through the holes. The holes may, for example, be arranged in a pattern along one side of the cement director 105, thereby allowing cement to flow preferentially out of one side of the cement director 105. Alternatively, the regions of greater permeability 125 may be regions including a more permeable material and/or a broader mesh.

In one embodiment, the cement director 105 may be constructed from a plurality of layers, with the regions of greater permeability 125 formed by removing one or more of the plurality of layers from one or more regions of the surface while leaving the other layer(s) in place. As such, the remaining layers can provide structural integrity to the cement director even if a portion of one or more other layers is removed to produce the regions of greater permeability 125.

Figure 10:
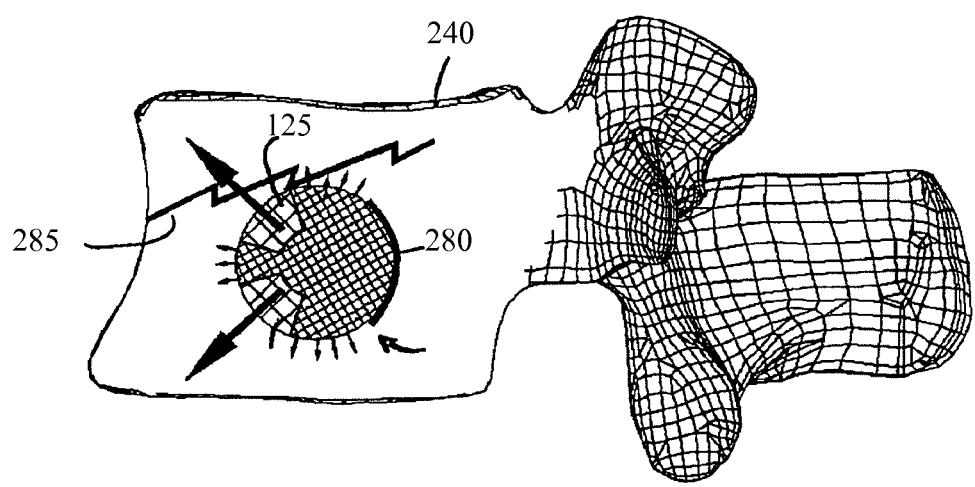
FIG. 10 is a schematic side view of a cement director for use in treating a vertebral fracture, in accordance with one embodiment of the invention.
Figure 11:
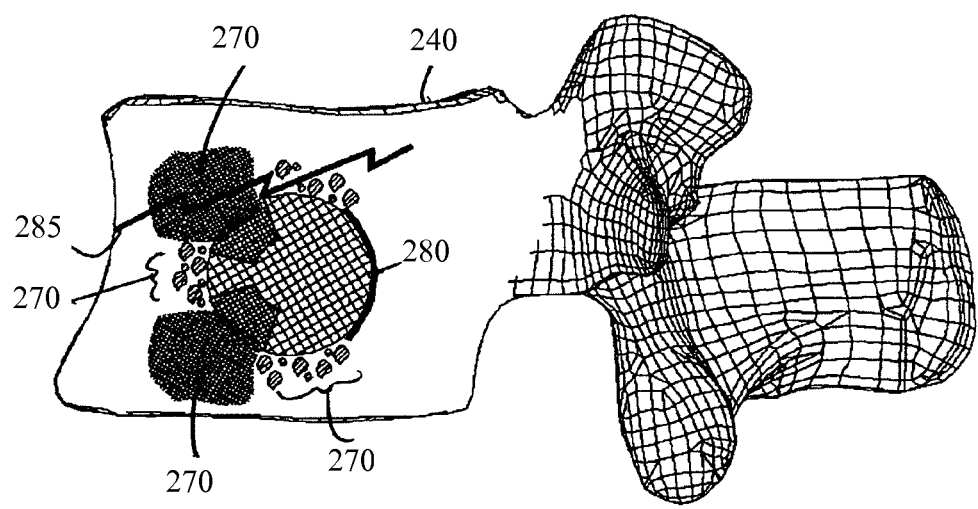
FIG. 11 is a schematic side view of the expanded cement director of FIG. 10 after injection of bone cement.
Figure 12:
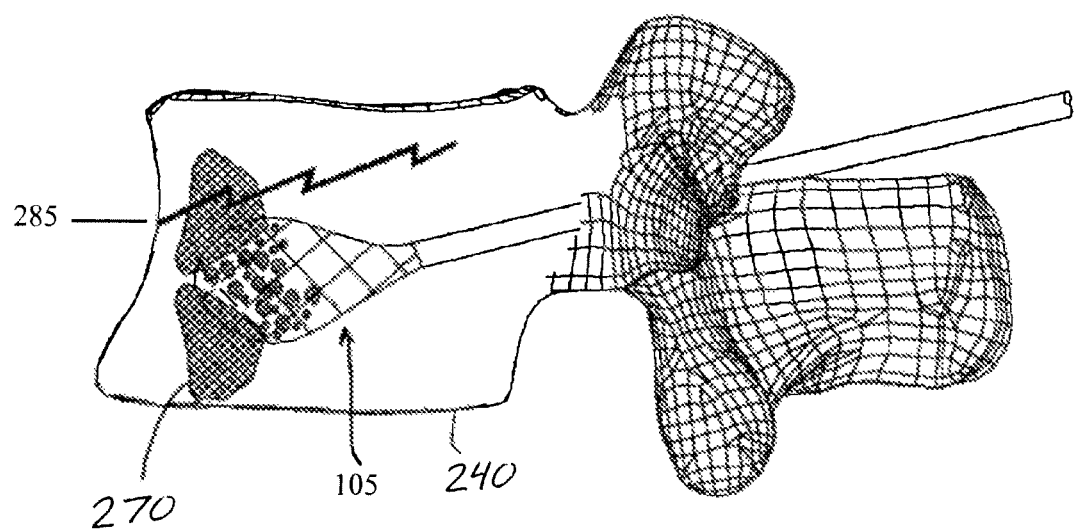
FIG. 12 is a schematic side view of another cement director for use in treating a vertebral fracture, in accordance with one embodiment of the invention.

The regions of greater permeability 125 may be used to ensure that bone cement exits from the cement director 105 in the required direction, i.e., to appropriate areas of the vertebral body to treat a fracture or other structural failure, such as an anterior-superior and/or anterior inferior region of a vertebral body. The regions of greater permeability 125 may be of any appropriate size and shape (e.g., circular, oval, and/or square) and may be arranged in any appropriate number and configuration. In one embodiment, the cement director 105 may include one or more baffled regions (as shown in FIGS. 10 and 11), with baffles 280 preventing flow of bone cement through the baffled regions. Example cement directors 105, and hole configurations therefor, are shown in U.S. patent application Ser. No. 11/957,039, filed Dec. 14, 2007, and U.S. Pat. No. 7,465,318, issued Dec. 16, 2008, which are incorporated herein by reference in their entireties.

In one embodiment, the cement director 105 may be expanded, or partially expanded, by a dilation balloon which is inserted into the interior of the cement director 105 either prior to, or after, insertion of the cement director 105 through a cannula and into the interior of a vertebral body. The inflation balloon may, for example, be a standard angioplasty balloon that may, for example, have a folded profile of less than about 2 mm. In one embodiment, the cement director 105 is positioned over the dilation balloon prior to insertion into a vertebral body, with a total cross-sectional diameter of the cement director 105 of less than about 4 mm, when in an unexpanded state. In one embodiment, the cement director 105, with the dilation balloon therein, is inserted through a cannula and into an interior of a vertebral body, or other appropriate treatment site, in an undeployed configuration. The dilation balloon is then expanded (e.g., by injection of a balloon expansion material such as a liquid, e.g., saline solution, through a fill passageway in the deployment system 110) to expand the cement director 105. The balloon is then withdrawn after dilatation, and cement is injected through the delivery system 110 and into the cement director 105. The cement director 105 is then detached from the delivery and deployment system 110. Alternatively, the balloon may be inserted into the interior of the cement director 105 after the cement director 105 has been inserted into a vertebral body. Using a balloon to assist in the expansion of the cement director 105 may be beneficial, for example, in allowing for improved controlled expansion of the cement director 105, with an increased expansion force than that available through a self-expanding device to allow for reconstruction of a collapsed osteopathic vertebral body including height restoration.

The balloon may be removed from the interior of the cement director 105 after expansion, but prior to cement injection. In an alternative embodiment, the balloon may be configured to burst, or be permeable, upon full expansion, thereby allowing the cement to be injected into the cement director 105, and to escape the cement director 105 through the regions of greater permeability 125, through the same fill passageway as the balloon expansion material, without the need to remove the balloon prior to cement injection. In a further alternative embodiment, the fill passageway for the cement may be separate from, and exterior to, the balloon, thereby allowing the cement to be injected into the interior of the cement director 105 but exterior to the balloon. As a result, the balloon may be left in the cement director 105 in an unexpanded state during cement injection.

Figure 2:
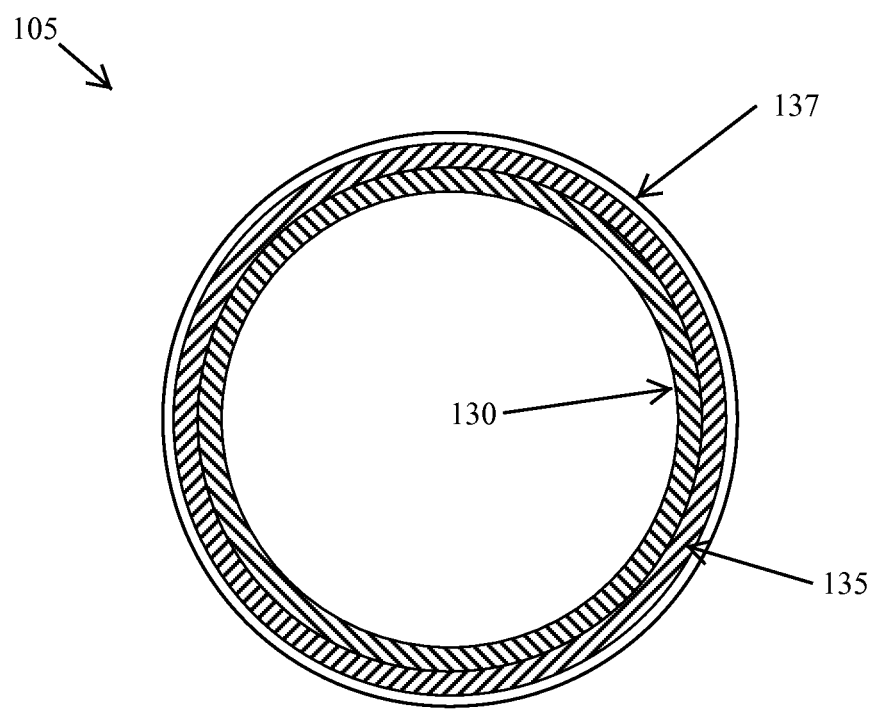
FIG. 2 is a schematic sectional end view of an example cement director, in accordance with one embodiment of the invention.
Figure 3:
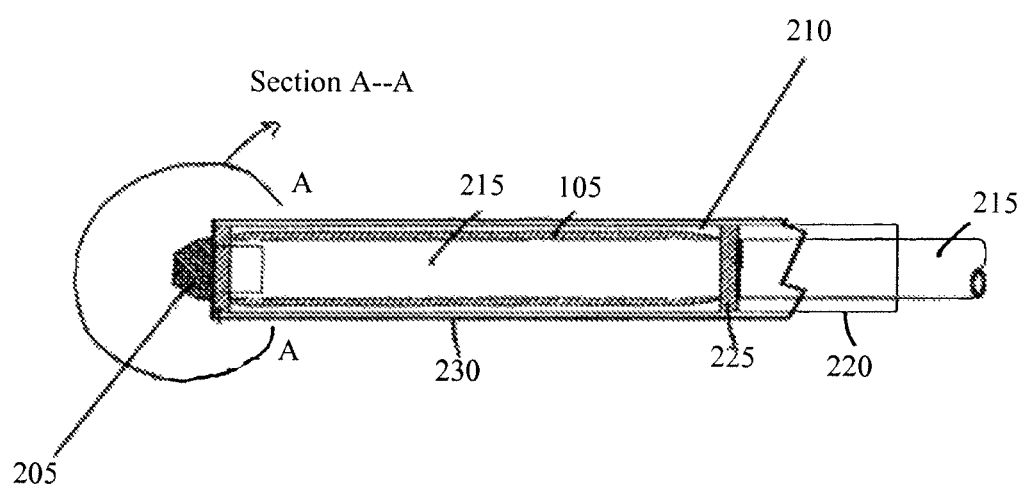
FIG. 3 is a schematic side view of a cement director attached to a deployment system, in accordance with one embodiment of the invention.
Figure 4:
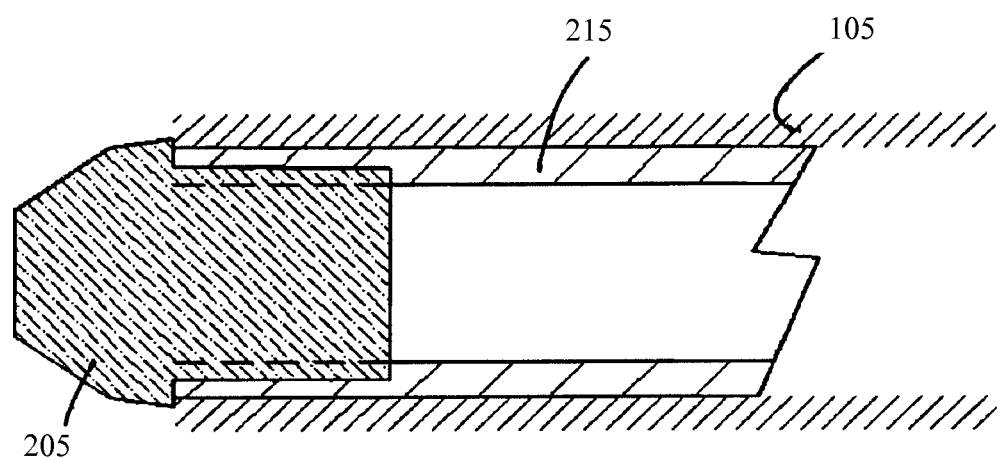
FIG. 4 is a schematic side view of the distal end of the cement director of FIG. 3 through section A-A.
Figure 5:
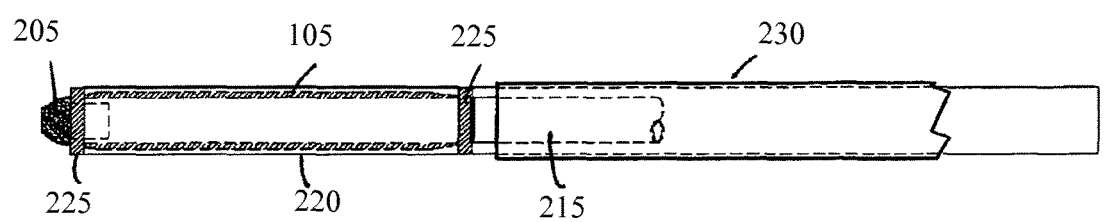
FIG. 5 is a schematic side view of the cement director of FIG. 3 exiting through a cannula, in accordance with one embodiment of the invention.

One embodiment of the invention includes a cement director 105 including a multi-layered mesh structure with two or more layers. An example multi-layered cement director 105, as shown in FIG. 2, includes two layers of a shape-memory material such as, but not limited to, Ni—Ti. The bi-layered cement director 105 includes an inner layer 130, formed, for example, from austenitic Ni—Ti, and an outer layer 135, formed, for example, from martensitic Ni—Ti. In one embodiment, the transition temperature from martensite to austenite of the inner layer 130 is less than a body temperature (e.g., less than about 100° F.), and the outer layer 135 has a transition from martensite to austenite greater than the body temperature. The bi-layered material may, for example, be fabricated into the cement director 105 shape such that the two layers can act in combination such that they can be releasably constrained to a shape smaller that the fabricated diameter, such that the cement director 105 will self expand to a predetermined shape when unconstrained and wherein the cement director 105 can be further enlarged by application of a force by deforming the outer martensite layer 135 without slip deformation or "yielding" to an enlarged diameter greater than the self-expanded diameter. The cement director 105 may, optionally, include a covering layer 137.

In one embodiment, a cement director having an austenite layer may be fabricated such that its original, undeformed, shape corresponds substantially with the required final balloon-expanded shape upon delivery of the cement director into a vertebral body. The austenite layer may then be elastically deformed to a collapsed configuration, and held in this collapsed configuration by a sheath and/or elongate rod, during insertion and prior to deployment. As such, upon removal of the sheath and/or elongate rod, the austenite layer will deform back to its original, undeformed, shape. In one embodiment, a martensite layer may be placed over or under, or interwoven within, the austenite layer. In operation, the martensite layer will try to hold its deformed shape upon a deformation of the cement director into a collapsed configuration and will, therefore, impede expansion of the austenite layer to its original, undeformed, shape. As a result, removal of the sheath and/or elongate rod will result in the cement director partially self-expanding (due to the elastic properties of the austenite layer), but not returning fully to the original, undeformed, shape (due to the martensite layer hindering the full self-expansion of the austenite layer). In this case, a balloon may be used to further expand the partially expanded cement director to return it to its fully expanded configuration (corresponding, or substantially corresponding, to the cement director's original, undeformed, shape).

By forming a cement director from both an austenite layer and a martensite layer, and expanding the cement director within the vertebral body to correspond in shape to the original, undeformed, shape of the cement director prior to collapsing the cement director for delivery, the cement director may provide a level of structural support for the vertebral body upon deployment, but prior to cement injection. More particularly, the austenite layer of the cement director will preferentially stay in its original, undeformed, shape, and will therefore provide a force hindering and subsequent deformation within the body. In addition, the martensite layer will impede any deformation from its shape, and therefore provide additional force hindering deformation of the cement director. As such, the cement director may provide a certain level of structural support for the vertebral body even before cement injection.

In one embodiment, a bi-layered cement director 105 may be inserted into an interior of a vertebral body with a balloon, or other appropriate expansion element, positioned within the interior of the cement director 105. A removable sheath may be placed over the cement director 105 to hold the cement director 105 in a collapsed, undeployed, state prior to insertion. A removable push rod may be pleased into the interior of the cement director 105 in addition to, or in place of, the sheath to assist in holding the cement director 105 in an undeployed state prior to insertion and/or curving of the cement director to conform to the cavity that has been created. Upon removal of the sheath and/or push rod, the bi-layered cement director 105 partially self-expands to a partially expanded shape smaller than the preset shape of the austenite shape memory material. The balloon can then be used to further expand the cement director 105 to a fully expanded state (which may, for example, conform substantially to the preset shape of the austenite layer 130), with the outer martensite layer 135 assisting in holding the cement director 105 in its expanded state after removal of the balloon. As the outer martensite layer 135 is selected such that the transition temperature from martensite to austenite is greater than the body temperature of the patient into which the cement director 105 is inserted, the outer martensite layer 135, and therefore the cement director 105, will hold its shape after deformation by the balloon. As the material has not yielded or undergone plastic deformation during expansion by the balloon, the predetermined, self-expanded shape of the cement director 105 is recoverable after expansion if the temperature of the outer martensite layer 135 exceeds the transition temperature, from martensite to austenite, for this material. However, as the material of the outer martensite layer 135 is selected such that the transition temperature is greater than body temperature (i.e. approximately 100° F.), this recovery will not happen during normal deployment and use.

In one embodiment, the cement director 105 is made from a shape-memory alloy that is super-elastic/pseudo-elastic. The term super-elasticity is used to describe the property of certain alloys that can be strained in their austenite state more than ordinary spring materials without being plastically deformed. This unusually large elasticity in the austenite state is called pseudoelasticity (because the mechanism is nonconventional in nature) or is called transformational superelasticity because it is caused by a stress induced phase transformation. Shape memory and superelasticity are particularly pronounced in Ni—Ti alloys. As a result, Ni—Ti stents created in the austenite crystal phase can be deformed by external force without plastic deformation or yielding. An example vascular stent including shape memory alloys is described in U.S. Pat. No. 6,451,052 to Burmeister et al., issued on Sep. 17, 2002, the disclosure of which is being incorporated herein by reference in its entirety. In an alternative embodiment, the cement director 105 may include, or consist essentially of, a material that may self-expand to a predetermined size upon initial deployment, and thereafter plastically deform upon further expansion by a balloon.

In various embodiments, the multi-layered cement director 105 may include any appropriate number of layers. For example, one embodiment of the invention may include a multi-layered cement director 105 including a single martensitic layer or a multi-layered martensitic material. In general, as discussed above, the martensite phase material will have a higher transition temperature than body temperature and may be pliable but stiff depending on the thickness. While the martensitic material retains is deformed shape after load removal (at temperatures below its transition temperature), martensitic deformation is caused by detwinning and not through typical plastic deformation or yielding of crystal slip. In various embodiments, the cement director 105 may be a stent that is austenite at room temperature or be entirely martensitic at room temperature.

In one embodiment, a cement director may be formed from a single layer mesh structure formed from a first shape memory material in a martensite phase at body temperature. The cement director may include a closed distal end, an open proximal end, and at least one region of different permeability to a bone cement. The martensite mesh structure is expandable from an unexpanded configuration to an expanded configuration by expansion of a balloon within an interior of the mesh structure, and is adapted to maintain the expanded configuration after removal of the balloon from the interior of the mesh structure. By using a martensite shape memory material, the cement director may be held in an unexpanded configuration without the need for a push rod and/or sheath, with the cement director being expanded to a deployed configuration through inflation of a balloon or actuation of other appropriate expansion element after insertion into the vertebral body.

Forming a cement director from a shape memory material in a martensite phase at body temperature may provide substantial advantages over cement directors formed from plastically deformable materials. For example, martensite shape memory material cement directors may provide for a ratio of expansion from an unexpanded to an expanded configuration significantly greater than that available for plastically deformable devices. In addition, use of martensite material may, in one embodiment, allow for overstretching of the cement director by a balloon, such that the cement director recoils to a predetermined diameter after removal of the balloon, leaving a space between the bone and the resting stent position. In this embodiment, bone cement could then fill the void left by the recoil of the cement director.

In one embodiment, the cement director 105 can be manufactured by creating a tube of mesh material out of the appropriate super-elastic Ni—Ti alloy. The tube may be laser cut into a stent like structure, with the distal end thereafter sealed, for example, by welding. Alternatively, the cement director 105 may be braided into a woven shape. In certain embodiments, a coating may be applied by dip coating or spraying. Alternatively, a coating may be applied over the struts over which a mesh structure is laminated to the cement director 105, and a further coating may optionally be applied to seal the mesh. The regions of greater permeability 125 may be holes cut, for example, by a hot tip soldering iron and/or by a laser.

An example manufacturing process may include creating a bi-layer Ni—Ti tube, as shown in FIG. 2, or single layer of super-elastic Ni—Ti, and laser cutting the tube into a stent like design. The stent is then formed into a cement director 105 by putting it into a fixture and rounding the ends, with the distal end 115 sealed, for example, into a ball like rounded end. The cement director 105 may be covered by a covering layer 137. For example, the cement director 105 may be dip-coated, for example with silicone, an elastomeric urethane, polyurethane, isobutylene, polyester, nylon, natural fiber material, and/or a styrene rubber, to seal the openings. The cement director 105 can also be covered with a nylon or polyester mesh than can be embedded into the elastomeric matrix and will move as the cement director 105 opens, as has been done in reinforced balloons. Holes may then be cut into the matrix covering the cement director 105 with a laser or hot tip device to create the regions of greater permeability 125. The unopened cement director 105 is now ready for releasably coupling to a delivery system 110, as shown in FIGS. 1A-1D.

In operation, the various cement directors 105 described herein may be used to treat a fracture, or other structural failing or weakness, in a vertebral body 240, as depicted in FIGS. 8-12. As discussed above, a cement director 105 may be releasably coupled to a delivery system 110 and inserted through a delivery cannula (i.e., a hollow channel inserted though the skin and into the target site within the patient to allow access for the cement director 105). The cement director 105 may be inserted into previously created curvilinear or straight cavities or paths created in the vertebral body 240 target site by one or more drilling and/or reaming device as described, for example, in U.S. patent application Ser. No. 11/957,022, filed Dec. 14, 2007, U.S. patent application Ser. No. 12/486,439, filed Jun. 17, 2009, and U.S. provisional patent application Ser. No. 61/210,771, filed Mar. 23, 2009, the disclosures of all of which are being incorporated herein by reference in their entirety. An example method of inserting and deploying the cement director 105 is shown in FIGS. 2-12.

As illustrated in FIG. 2-7, the cement director 105 may have a closed distal end 205 and an open end 210, with the cement director 105 collapsed over a hollow push rod 215 prior to inserting the cement director 105 into a catheter sheath 220, so that the push rod 215 is effectively releasably linked to the closed end 205 of the cement director 105. (The catheter sheath may, itself, include radio opaque marker bands 225). The proximal open end 210 is releasably coupled to a distal end of the deployment device. The hollow push rod 215 facilitates placement of the collapsed, enclosed mesh structure into the cavity, via a cannula 230, through its removable connection to the closed end 205 of the cement director 105. The releasable connection may be a mechanical linkage, such as a thread or luer lock, a press-fit connection, or any other form of releasable engagement. Alternatively, the push rod may be positioned in the cement director without being coupled to the distal end 205.

In one embodiment, during constraint of the cement director 105 in the sheath 220, the austenite layer 130 may stress induce to a martensitic state. In the alternative, the cement director 105 may be cooled below the transition temperature of layer 130 to facilitate its deformation and constrainment. The martensitic layer 135 merely undergoes reversible deformation and the cement director 105 may be loaded into the sheath 220. However with temperature changes occurring up to body temperature, layer 130 will remain martensitic until the constraint is removed. When released in place in the vertebral body 240 it will expand to its self expanded state, e.g., about 10 mm, 15 mm, or a percentage thereof, due to the transformation of layer 130 from martensite to austenite.

Figure 6:
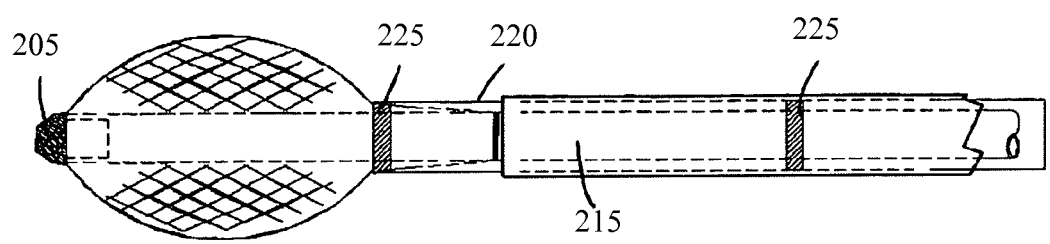
FIG. 6 is a schematic side view of the cement director of FIG. 3 after expansion, in accordance with one embodiment of the invention.
Figure 7:
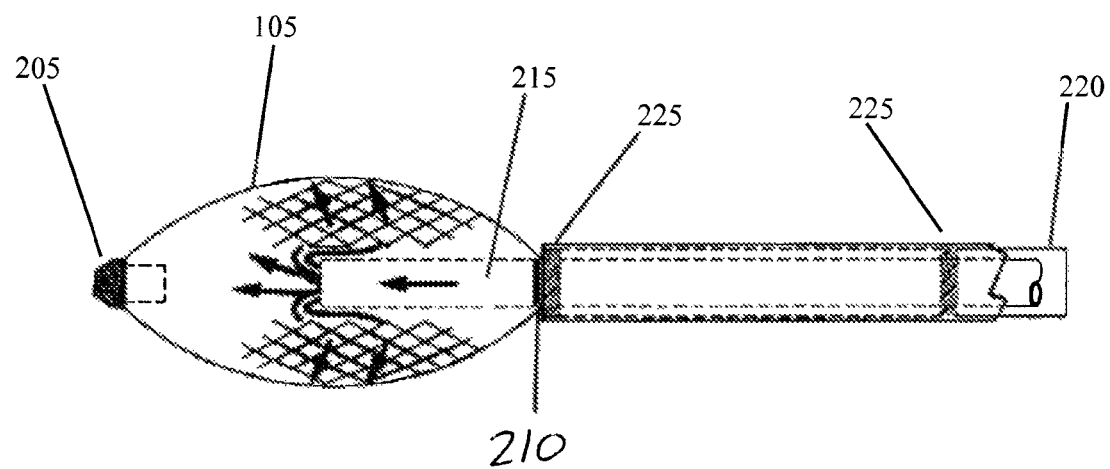
FIG. 7 is a schematic side view of the expanded cement director of FIG. 6 during cement injection, in accordance with one embodiment of the invention.

Once the cement director 105 is fully inserted into the cavity formed within the bone structure being treated, the sheath 220 is retracted, as illustrated in FIG. 6, and the self-restoring cement director 105 expands to its final shape, as illustrated in FIGS. 6 and 7. The self-expanding cement director 105 can self-expand to a first diameter of, for example, about 10 mm. If the physician deems it appropriate, or if the structure has not expanded fully, a balloon catheter can be inserted into the delivery system 110 through the hollow push rod 215 into the interior of the cement director 105. The balloon can, for example, be an angioplasty balloon catheter as commonly used in peripheral balloon angioplasty, and is capable of expanding to up to about 10, 12, or even 15 mm, or greater. The balloon may then be expended through injection of an expansion fluid, e.g., a saline solution, under fluoroscopic guidance to achieve the distraction of the endplates shown in FIGS. 10 and 11.

The releasable connection between the closed end 205 of the cement director 105 and the push rod 215 (see FIG. 4) may be severed, and the hollow push rod 215 may be partially retracted until its tip is located generally in the center of the cement director 105, at which point the push rod 215 may, in certain embodiments, be used secondarily as a cement injector. In an alternative embodiment, the push rod 215 may be a solid element which removably extends through a hollow cement injector passageway.

A filling portal (not shown) on the other end of the rod 215 is then connected to a cement injection syringe via, for example, a luer lock fitting. Cement can then be injected into the center of the cement director 105, as indicated by the directional arrows shown in FIG. 7. In one embodiment, the open end 210 of the cement director 105 can be collapsed around the hollow push rod 215, thereby forming a slideable connection that assures lengthwise positioning and targeting of the flow portal of the push rod 215 within the center axis of the cement director 105 and easy removal of the push rod 215 after filling with cement.

Figure 8:
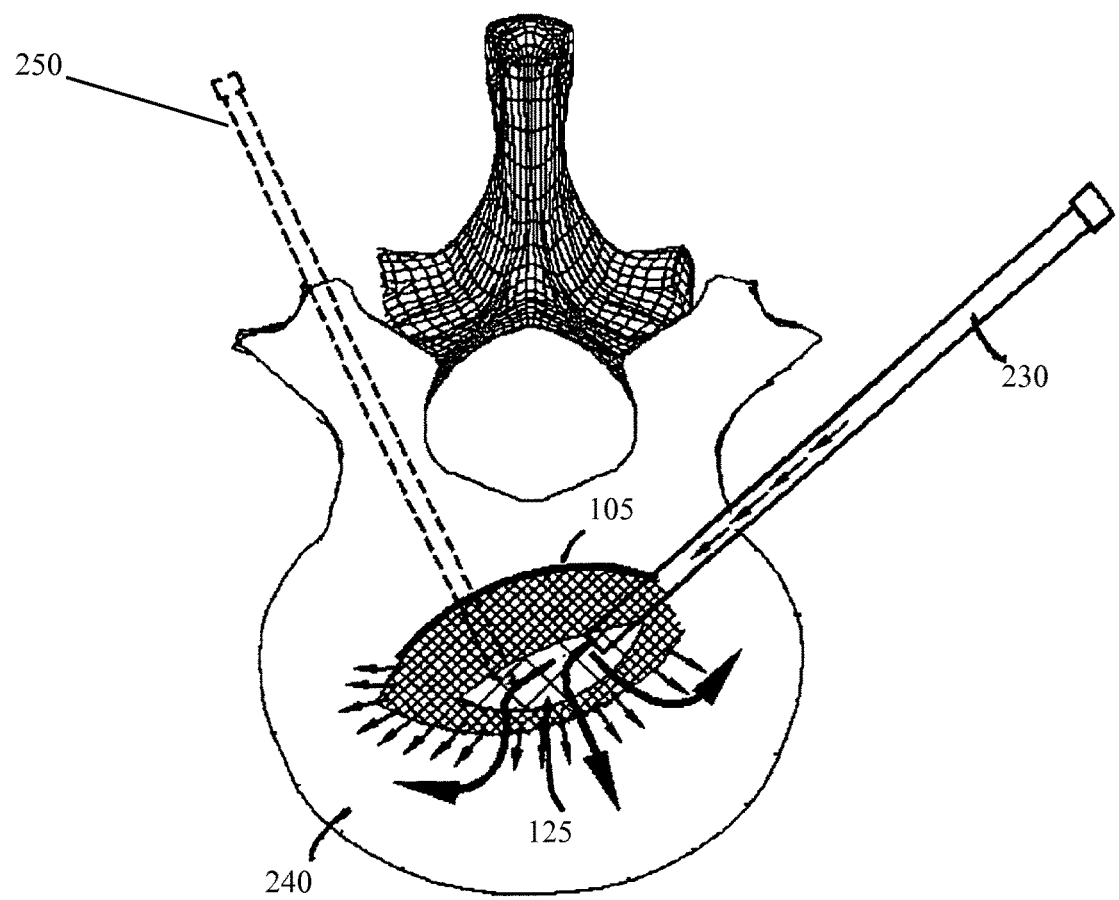
FIG. 8 is a schematic top view of the expanded cement director of FIG. 6 during cement injection, placed in a vertebral body, in accordance with one embodiment of the invention.
Figure 9:
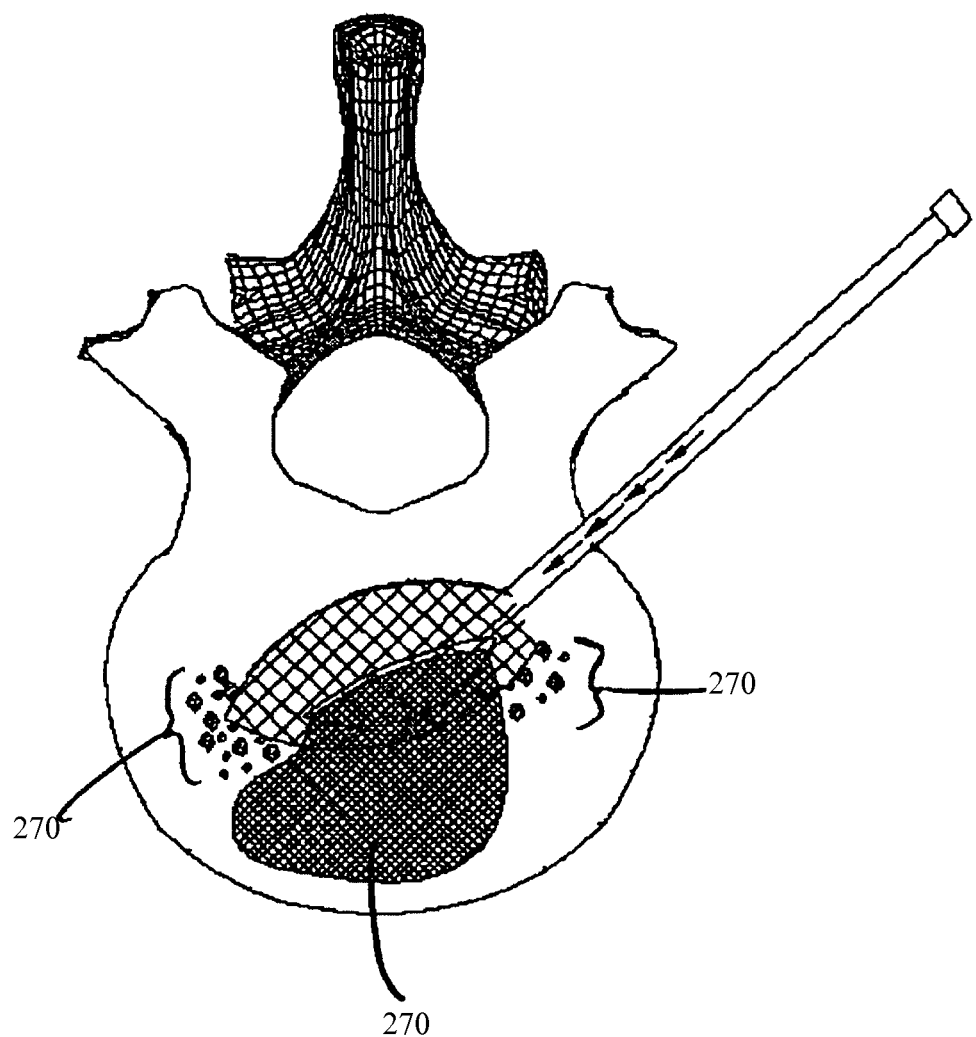
FIG. 9 is a schematic top view of the expanded cement director of FIG. 8 after cement injection, in accordance with one embodiment of the invention.

In an alternative embodiment, as shown in FIG. 8, a separate filling needle 250 capable of penetrating the mesh structure of the cement director 105 may be used to perforate the meshwork after deployment of the cement director 105 in the bone cavity, so that the cement injection is not restricted to any particular vector; indeed, the cement director 105 may, in various embodiments, be filled in one or more orientations at one or more points of entry. By perforating the outer mesh, the needle flow portal 250 may be placed in the center of the cement director 105 or, if necessary, entirely through the cement director 105 to regions of the bone external to the cement director 105 where it may be desirable to inject additional cement directly into a bone fracture site.

As illustrated in FIGS. 8-12, the regions of greater permeability (e.g., holes) 125 control the direction of flow of cement into the vertebral body 240 into which the cement director 105 is inserted. In particular embodiments, a greater amount of cement will flow out of the holes 125 as represented by the relatively thick, large arrows, than will flow out of the remainder of the cement director 105, as represented by the relatively thin, small arrows. Alternatively, the cement director 105 may be configured to allow cement to flow only out of the holes 125.

For a given orientation of the cement director 105 within the vertebral body 240, with the holes 125 facing, for example anterior-superior and anterior-inferior, significant volume of cement may be directed anterior-superior and anterior-inferior into the forward third of the vertebral body 240, thereby forming "mantles" 270 of cement which cross the plane of the vertebral fracture 285. The cement mantles 270 may be located adjacent to the vertebral endplates and thus will form a loadbearing column of cement, as shown, for example in FIGS. 11 and 12. By carefully directing the cement out through the holes 125 only in the appropriate direction and away from more delicate regions of the vertebral body 240, these cement mantles may be safely formed without endangering the patient.

In one embodiment, the cement director 105 is an at least partially balloon-expandable cement director made, at least in part, of martensitic Ni—Ti. In this case, the cement director 105 may be attached to the hollow push rod 215 in its collapsed state. After the cement director 105 is inserted into the cavity formed within the bone structure 240, a balloon, e.g., a peripheral angioplasty balloon that may have a profile of less than about 2-3 mm, may be inserted through the push rod 215 into the collapsed cement director 105. When the cement director 105 is fully inserted into the cavity, the balloon may be expanded and the cement director 105 may thereby expand to its final deployed shape. The balloon catheter may be deflated and withdrawn from the push rod 215 so that cement can be injected into the cement director 105 and out through the holes 125 into the vertebral body 240 at the appropriate locations.

In various embodiments, the cement director 105 may be formed to have a substantially cylindrical shape (see, for example, FIGS. 1A-1D) or an ovoid shaped form upon expansion (see, for example, FIGS. 6-9). In alternative embodiments, other shapes may be desirable for the expanded cement director 105 shape. For example, an oblong or pear-shaped cement director 105 might be desired when, for example, it is clinically desirable or necessary to approach the vertebral body 240 bilaterally, through each pedicle, as illustrated, for example, in FIG. 12. Alternatively, a relatively thin cement-directing structure may be employed for spinal fusion techniques, wherein the cement-directing structure is deployed through minimally invasive means into the disc space to provide support to the spinal column following discectomy. In certain embodiments, the cement director 105 may be formed to follow a curvilinear pathway formed in a vertebral body, upon expansion.

In addition, various embodiments of the invention may include a cement director 105 formed from a braided mesh structure. In alternative embodiments, self-expanding, collapsible mesh structures can be formed by a variety of other techniques including, but not limited to, laser-cutting tubes.

It should be understood that alternative embodiments, and/or materials used in the construction of embodiments, or alternative embodiments, are applicable to all other embodiments described herein.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A system for treating a vertebral body comprising:
a delivery device comprising a distal end configured for insertion into a vertebral body and a proximal end comprising a handle, wherein the delivery device includes a fill passageway;
an expandable device configured to be releasably coupled to the distal end of the delivery device, the expandable device comprising a mesh structure comprising a plurality of layers including a first layer comprising a first shape memory material in an austenite phase at body temperature and a second layer comprising a second shape memory material in a martensite phase at body temperature, wherein by forming the mesh structure with the austenite layer and a martensite layer, the mesh structure is configured to correspond in shape to an original undeformed shape of the mesh structure prior to collapsing the mesh structure for delivery, the mesh structure provides structural support for the vertebral body upon deployment and prior to cement injection, and
a balloon configured to be coupled at the distal end of the delivery device and adapted to further expand the expandable device from the original undeformed shape of the mesh structure when disposed therein in order to provide an enlarged cavity for cement injection, wherein the balloon is configured to expand upon introduction of balloon expansion material from the fill passageway of the delivery device, wherein the expandable device is configured to receive bone cement from the fill passageway of the delivery device, wherein the mesh structure further includes a third layer surrounding the first layer and the second layer, wherein the mesh structure is configured to expand to a partially expanded shape smaller than the original undeformed shape after deployment and the balloon is configured to expand the mesh structure from the partially expanded shape to an expanded form, and wherein the mesh structure is configured to maintain the expanded form upon deflation of the balloon and the balloon is configured to be removable from the mesh structure.

2. The system of claim 1 further comprising a push rod adapted to be removably insertable through the delivery device and into the expandable device to hold the expandable device in a collapsed configuration prior to deployment.

3. The system of claim 1 further comprising a sheath adapted to removably extend through the delivery device and over the expandable device to hold the expandable device in a collapsed configuration prior to deployment.

4. The system of claim 1, wherein the mesh structure is generally cylindrical in shape, when expanded, such that an outer diameter along at least a portion of a length of the mesh structure is substantially constant.

5. The system of claim 1, wherein the mesh structure includes at least one region of greater permeability relative to a second region of lesser permeability.

6. The system of claim 5, wherein the region of greater permeability includes a plurality of holes positioned along a length of the mesh structure.

7. The system of claim 1, wherein the third layer is a covering layer.

8. The system of claim 7, wherein the mesh structure includes at least one region of greater permeability relative to a second region of lesser permeability, and the region of greater permeability comprises a region that is not covered by the covering layer.

9. The system of claim 7, wherein the covering layer is impermeable to bone cement.

10. The system of claim 7, wherein the covering layer comprises an elastic material.

11. The system of claim 10, wherein the elastic material is selected from the group consisting of silicone, polyurethane, styrene, isobutylene, polyester, nylon, natural fiber material, and combinations thereof.

12. The system of claim 1, wherein at least one of the first and second shape memory materials comprises nickel titanium.

13. The system of claim 1, wherein the expandable device includes a closed distal end and an open proximal end.

14. The system of claim 13, wherein the open proximal end of the expandable device is configured to be releasably coupled to a distal end of the fill passageway in the delivery device.

15. The system of claim 1 further comprising at least one of a drilling device and a reaming device configured to form a path or a cavity in the vertebral body.

16. A system for treating a vertebral body comprising:
a delivery device comprising a distal end configured for insertion into a vertebral body and a proximal end comprising a handle, wherein the delivery device includes a fill passageway;
an expandable device configured to be releasably coupled to the distal end of the delivery device, the expandable device comprising a mesh structure comprising a plurality of layers including a first layer comprising a first shape memory material in an austenite phase at body temperature and a second layer comprising a second shape memory material in a martensite phase at body temperature, wherein the mesh structure includes at least one region of greater permeability relative to a second region of lesser permeability, and
a balloon configured to be coupled at the distal end of the delivery device and adapted to further expand the expandable device from the original undeformed shape of the mesh structure when disposed therein in order to provide an enlarged cavity for cement injection, wherein the balloon is configured to expand upon introduction of balloon expansion material from the fill passageway of the delivery device,
wherein the expandable device is configured to receive bone cement from the passageway of the delivery device,
wherein the mesh structure further includes a third layer surrounding the first layer and the second layer,
wherein the mesh structure is configured to expand to a partially expanded shape smaller than the original undeformed shape after deployment and the balloon is configured to expand the mesh structure from the partially expanded shape to an expanded form, and
wherein the mesh structure is configured to maintain the expanded form upon deflation of the balloon and the balloon is configured to be removable from the mesh structure.

17. The system of claim 16, wherein the region of greater permeability includes a plurality of holes positioned along a length of the mesh structure.

18. The system of claim 16, wherein the expandable device is collapsible to a collapsed state and expandable to an expanded state by inflating the balloon within the expandable device.

19. The system of claim 16 further comprising a push rod adapted to be removably insertable through the delivery device and into the expandable device to hold the expandable device in a collapsed configuration prior to deployment.

20. The system of claim 16 further comprising a sheath adapted to removably extend through the delivery device and over the expandable device to hold the expandable device in a collapsed configuration prior to deployment.

* * * * *